US00PP11367P

United States Patent [19]

Luby et al.

[11] Patent Number: Plant 11,367

[45] Date of Patent: Apr. 25, 2000

[54] APPLE TREE CALLED 'MINNEWASHTA'

[75] Inventors: James J. Luby, Saint Paul; David S. Bedford, New Germany, both of Minn.

[73] Assignee: Regents of the University of Minnesota

[21] Appl. No.: 08/978,253

[22] Filed: Nov. 25, 1997

[51] Int. Cl.[7] ..... A01H 5/00

[52] U.S. Cl. ..... Plt./161

[58] Field of Search ..... Plt./34.1, 161

[56] References Cited

U.S. PATENT DOCUMENTS

P.P. 7,197 3/1990 Luby et al. ..... Plt./34.1

*Primary Examiner*—Howard J. Locker

*Assistant Examiner*—Melissa L. Kimball

*Attorney, Agent, or Firm*—Mueting, Raasch & Gebhardt, P.A.

[57] ABSTRACT

An apple tree having a somewhat upright form with vigorous growth in early years and attaining a spur-type habit with moderately vigorous growth as it matures, good hardiness with little winter injury, and annual fruit production. The fruit, which ripens early in the season yet can be stored for a relatively long period of time, has a well-balanced flavor, crisp and juicy texture, and pleasing exterior color and pattern.

4 Drawing Sheets

BACKGROUND OF THE INVENTION

Minnewashta is a new distinct variety of apple tree (*Malus domestica*) that is notable for its upright form with vigorous growth in early years and spur-type habit with moderately vigorous growth as it matures, its cold hardiness, and for bearing fruit annually. The fruit, which ripens early in the season yet can be stored for a relatively long period of time, has a well-balanced flavor, crisp and juicy texture, and pleasing exterior color and pattern. It was discovered by Applicant in 1986 as part of the University of Minnesota apple breeding program to develop witnter-hardy varieties with high fruit quality.

BRIEF DESCRIPTION OF THE PHOTOGRAPHS

The accompanying photographs are typical specimens of the trees of the variety and the fruit and flowers thereof as depicted in color. All photographs were taken at the University of Minnesota Horticultural Research Center near Excelsior, Minn. References to color relate to The Royal Horticultural Society (R.H.S.) Colour Chart noted herein as R.H.S. except for color terms of ordinary dictionary meaning which may occasionally be referred to. Measurements of size were recorded in 1996 at the Horticultural Research Center.

Origin of the Variety

Figure 1:
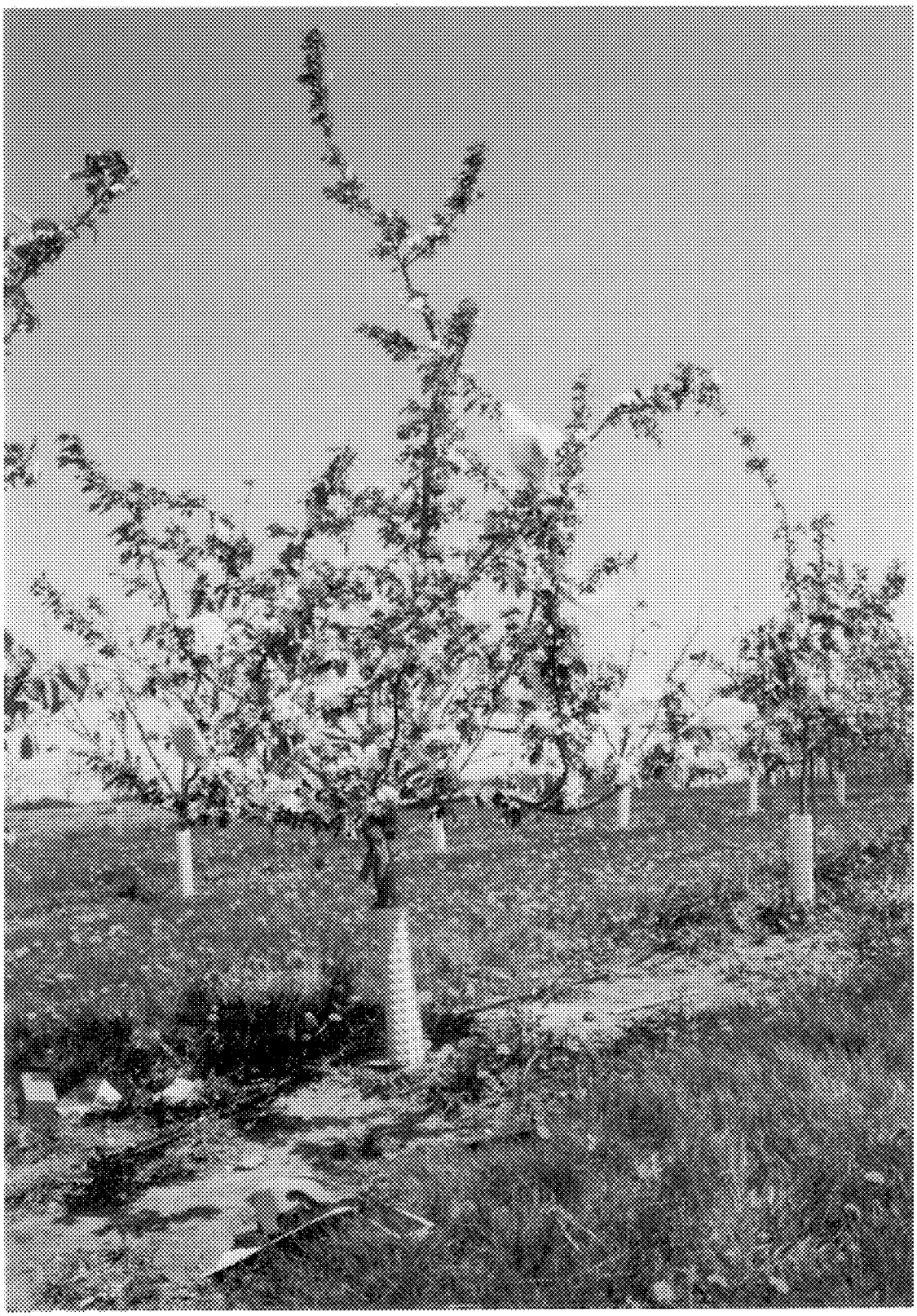
FIG. 1 shows a six year old tree of the variety.
Figure 2:
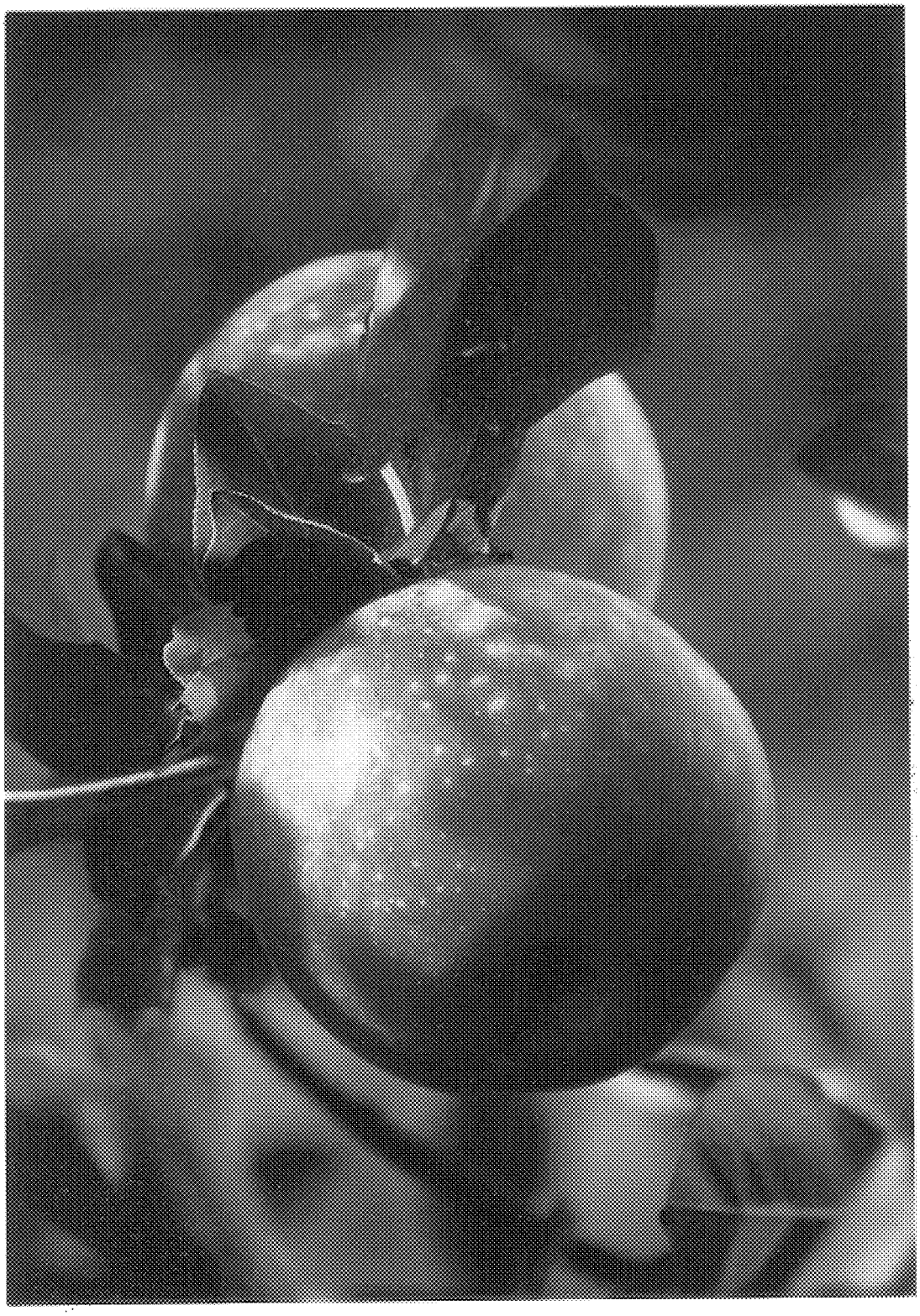
FIG. 2 shows fruits of the variety on the tree showing their coloration and shape and other characteristics.
Figure 3:
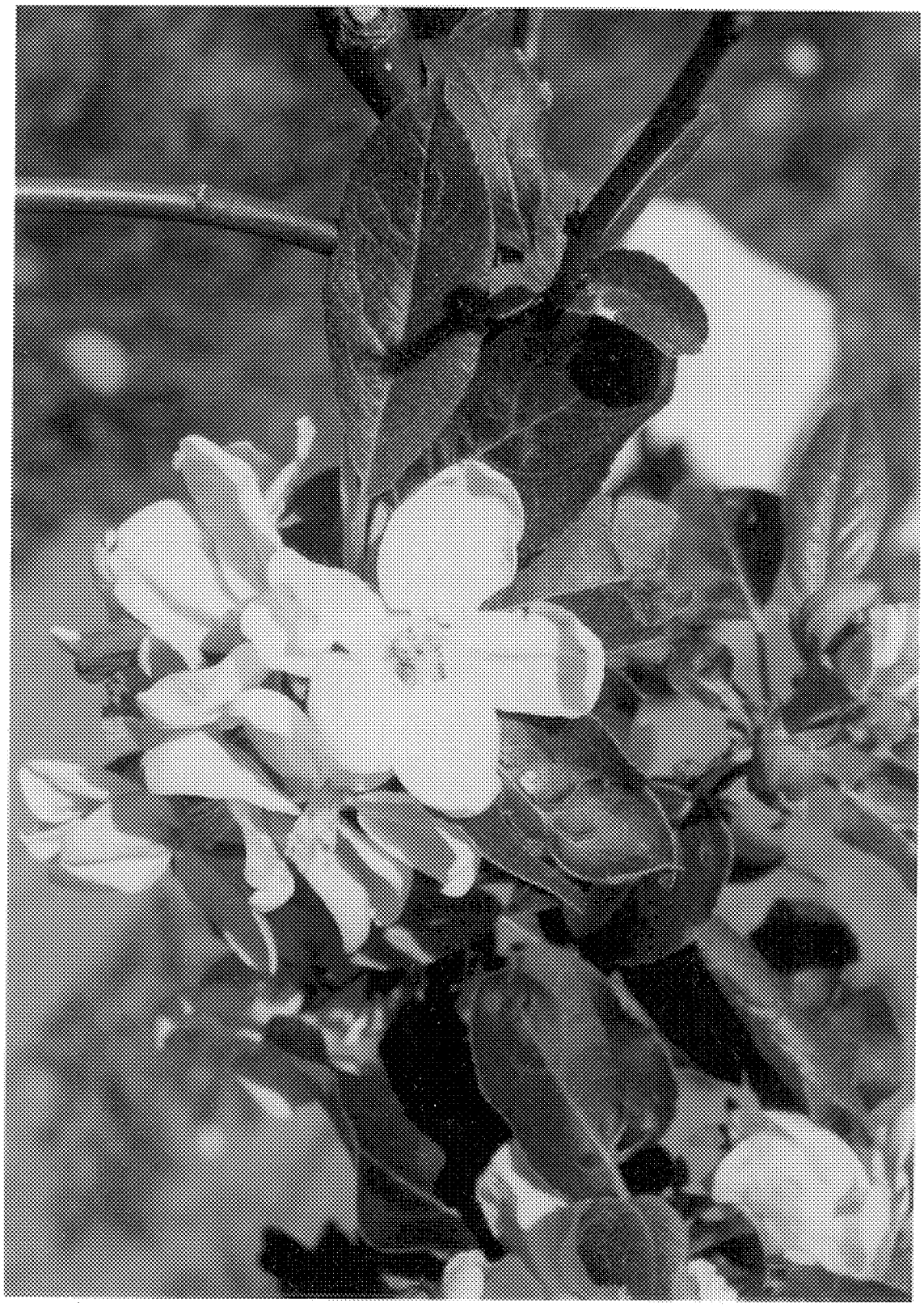
FIG. 3 shows open flowers of the variety.
Figure 4:
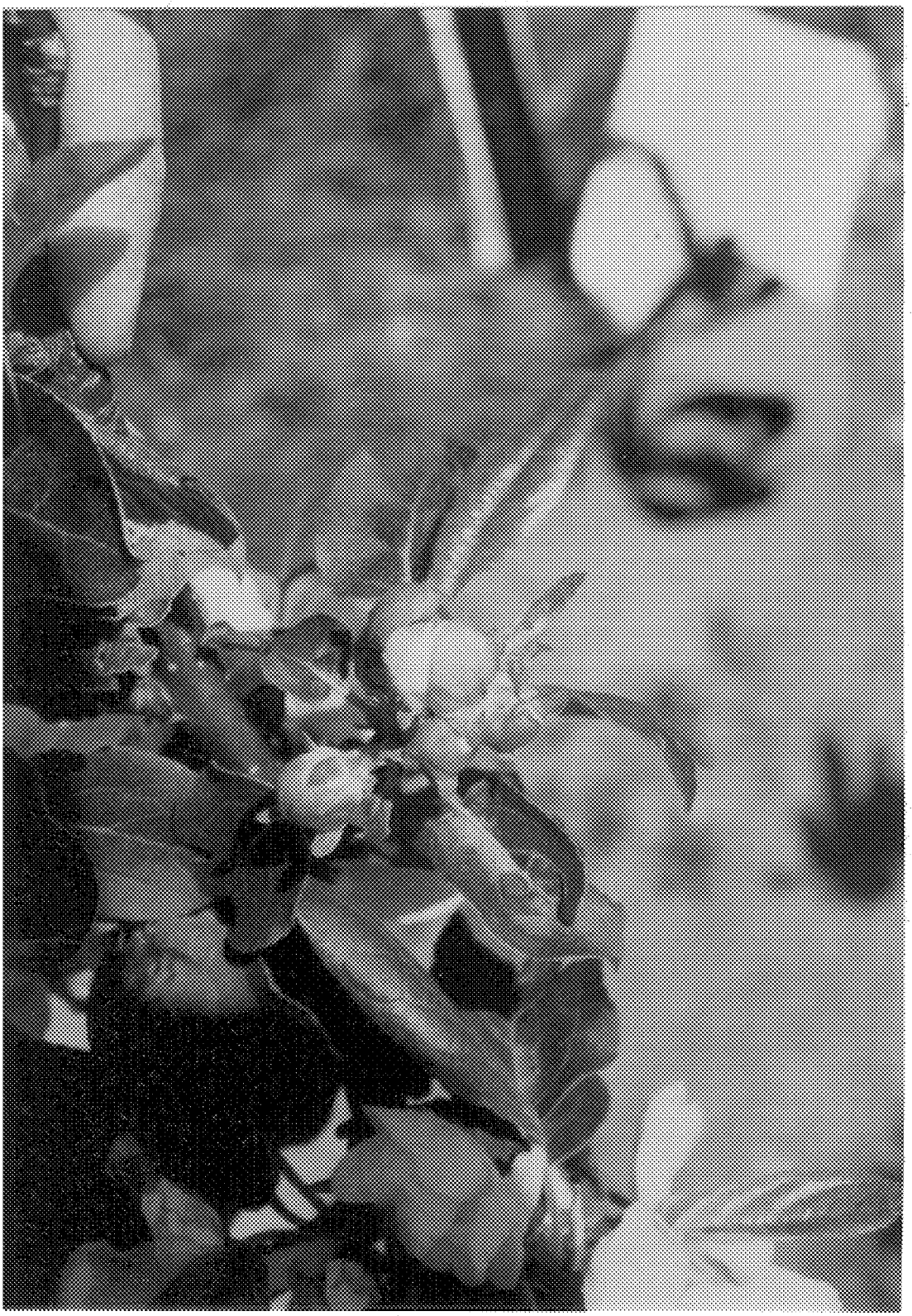
FIG. 4 shows flowers in the "balloon" stage before opening showing their coloration.

This new variety is a seedling of known parentage planted in 1974 as Tree 132 in Row 15 of Block 66 at the University of Minnesota Horticulltural Research Center, located in Carver County near Excelsior, Minn. The variety was produced from a cross designated AE 7214 that was made in 1972 between 'State Fair' (an unpatented variety) and MN 1691, an unnamed selection. Following discovery of the own-rooted original tree and asexual reproduction by grafting onto malling 26 rootstock, it was further tested as Minnewashta. The new cultivar has been asexually reproduced by means of budding and grafting at the Horticultural Reseach Center. Off-types, variants and mutations have not been observed.

Detailed Description of the Variety

The following traits have been repeatedly observed and are believed to be characteristics of this cultivar which, in combination, distinguish this apple tree as a new and distinct cultivar.

Tree: The new variety is characterized by a tree form that is somewhat upright with vigorous growth in early years, and attains a spur-type habit with moderately vigorous growth as it matures. The height of original tree is approximately 14 feet (4.27 meters) and the width is approximately 9 feet (2.74 meters). In the field at the Horticultural Research Center, the variety has exhibited little winter injury and has produced annual crops rated from moderate to heavy from 1990 through 1996 (Table 2). Injury to the stems and fruiting spurs has been minimal. Winter injury to Minnewashta is similar to other varieties that are adapted to this area, such as 'Haralson' and 'State Fair' (both unpatented cultivars). 'MacIntosh' and 'Golden Delicious' (both unpatented cultivars), varieties that are not commercially widely grown in this area, exhibit more winter injury compared to Minnewashta. Minnewashta trees have exhibited average precocity. Compared to other varieties tested, Minnewashta has average susceptibilty to apple scab and moderate resistance to fireblight in greenhouse tests. Dormant one-year old shoots lack pubescence, and are moderately shiny. The internodes are two-to-three cm long in the middle part of the dormant one-year old shoot. Lenticels are medium in number and size on one-year old shoots. The bark color of one-year old shoots on the sunny side is a grayed-orange corresponding to 165B on the R.H.S. Colour Chart. The lateral buds on one-year old shoots are medium-to-large and the bud tip is rounded. The lateral bud is adpressed to the axis of the stem.

Leaves: The leaves at the tip of the growing young shoot are densely pubescent giving them a whitish appearance. The shoot tip leaves are usually convex or, occasionally, concave. They are weakly to moderately pubescent on the upper side, light green in color correspopnding to 146A of the R.H.S. Colour Chart, and strongly pubescent on the lower side giving them a whitish-green appearance corresponding to 147B of the R.H.S. Colour Chart. The leaves are entire and not lobed, have an outward orientation from the stem, small stipules, a mucronate apex, crenate indentation of the margins and a weak-to-medium glossiness on the upper side. Fully expanded leaves have moderate pubescence on the lower side and light green color corresponding to 147B on the R.H.S. Colour Chart. The upper side of the expanded leaf is medium green corresponding to 147A. The veins and interveinal areas of the leaves have no anthocyanin coloration. For fully expanded leaves the mean petiole length is 2.40±0.04 cm, the mean blade length is 9.02±0.16 cm and mean blade width (at the widest expanse) is 4.34±0.11 cm.

Flowers: The bloom period is relatively early in the season, approximately two days before 'State Fair' and 'Paulared' (an unpatented cultivar) (approximately early to mid-May at Excelsior, Minn.). The color of the petals when flower is in the full balloon stage is medium pink corresponding to 67D of the R.H.S. Colour Chart. The pedicel is green. The flower is single having typically five petals (occasionally four or six) and mean diameter of 61.9±4.0 mm (range 56–70 mm). The petals are ovate in shape and generally overlapping one another when the flower is fully open. The petals have a mean length of 31.0±1.4 mm (range 29–32 mm) and a mean width of 20.6±1.1 mm (range 19–22 mm). The colors of the upper and lower sides of the petal when the flower is fully open are shades of white corresponding to 155D and 186D of the R.H.S. Colour Chart. As the flower matures, the upper side of the petal fades to a shade of white corresponding to 155B on the R.H.S. Colour Chart.

Fruit: The variety is notable for its early season of fruit ripening, with the fruit characterized by a combination of excellent flavor and crispness. It has been rated highly in tests with sensory evaluation panelists over ten years. The flovor is well balanced in acid and sugar content, and tasting more sweet that tart. The flesh is medium in firmness with a pressure at harvest ranging from 12 to 19 pounds. The flesh is crisp and juicy, and when chewed, has a sensation on the tongue of neither excessive coarseness or fineness. In tests between 1986 and 1996, sensory evaluation panels consistently rated it more highly for flesh texture (i.e., mouthfeel), flavor, and overall liking than other early season varieties grown in Minnesota such as 'Paulared', 'State Fair', 'Wealthy', and 'Gala' (all unpatented cultivars), and often rated it more highly than varieties harvested later in the season such as 'Sweet Sixteen', 'MacIntosh', 'Haralson', 'Regent' (all unpatented cultivars), 'Honeycrisp' (U.S. Plant Pat. No. 7,167) 'Honeygold', 'Fireside', and 'Connell Red' (unpatented cultivars) (Table 1). Overall, the fruit are high quality, i.e., pleasing exterior color and pattern, a crisp and juicy texture, and a pleasing flavor. The fruit are globose (blocky round) in shape and have an average diameter of approximately eight cm. They are assymetric in shape and are absent of ribbing. They are absent of crowning at the distal end. The aperture of the eye (calyx vestige) is closed and size of the eye is small. The calyx is persistent in mature fruit and the sepals are medium in length and touching at the base. The calyx basin is medium in depth and width. The pedicel, or stalk, is moderately thin and short (1.8 mm by 12 mm). The stalk cavity is medium in width. The surface of the fruit is smooth and has light bloom. The skin has slight waxiness and is medium in thickness. The ground color of the skin is grayed yellow to yellow corresponding to 160A or 160B to 11C, respectively, of the R.H.S. Colour Chart. Overall, fifty-to-eighty percent of the color of the skin is red stripe (streak), corresponding to 45A to 45B on the R.H.S. Colour Chart, depending on the exposure to the sun. The flesh color is cream, but is prone to oxidative browning when the fruit is cut. Russeting is absent or minimal and, if present, is restricted to the stalk cavity. The lenticels are large and prominent. In a median cross-section through the locules, the core line is weakly distinct and the locules are open. The seed is brown in color and normal in shape.

Fruiting: Trees of the variety bear fruit annually as a crop. Production is rated moderate to heavy, and has been observed on the trees every year from 1986 through 1997. The fruit ripens in late August at Excelsior, Minn., approximately one week after 'State Fair' and with 'Paulared'. The fruit have medium persistence on the tree, i.e., are not prone to premature dropping, and can usually be harvested in one or two pickings. In trials at the University of Minnesota Horticultural Research Center, the storage life of the fruit of Minnewashta without atmosphere modification is longer compared to other varieties that mature at nearly the same time during the season. The storage life of Minnewashta fruit is approximately seven weeks, whereas 'Redfree' and 'Summered' (both unpatented cultivars), for example, have a storage life of four weeks, five weeks for 'State Fair' and 'Paulared', and six weeks for 'Wealthy' and 'MacIntosh' (Roger's Red strain) (unpatented cultivars).

TABLE 1

Sensory Evaluations of Apple Varieties by Trained Panelists. Fruit were harvested at the University of Minnesota Horticultural Research Center. Each variety was rated by 14–20 panelists every year using a scale from 9 = excellent to 1 = very poor for each trait.

| Variety | Appearance | Skin texture | Flesh texture | Flavor | Flesh color | Overall liking |
|---|---|---|---|---|---|---|
| 1996 | | | | | | |
| Minnewashta | 7.5 | 6.5 | 7.0 | 7.2 | 7.3 | 7.2 |
| Paulared | 6.2 | 4.9 | 5.4 | 5.2 | 8.5 | 4.5 |
| Wealthy | 6.5 | 5.1 | 5.8 | 5.4 | 6.7 | 5.7 |
| Sweet Sixteen | 6.6 | 6.2 | 6.7 | 6.1 | 8.3 | 6.0 |
| Liberty | 7.4 | 6.1 | 6.5 | 6.9 | 6.2 | 6.6 |
| Honeycrisp | 8.0 | 6.8 | 7.5 | 7.0 | 7.4 | 7.4 |
| Regent | 7.1 | 5.2 | 6.6 | 6.3 | 6.0 | 6.3 |
| Keepsake | 4.6 | 6.0 | 6.3 | 6.9 | 6.2 | 5.9 |
| 1995 | | | | | | |
| Minnewashta | 7.8 | 7.3 | 7.3 | 7.6 | 7.4 | 8.1 |
| State Fair | 7.4 | 5.8 | 5.3 | 5.6 | 6.5 | 5.8 |
| Paulared | 5.8 | 5.5 | 6.1 | 5.1 | 7.1 | 5.4 |
| Wealthy | 7.9 | 6.1 | 7.1 | 6.5 | 7.6 | 6.9 |
| Honeycrisp | 6.9 | 6.6 | 7.5 | 7.2 | 7.1 | 7.5 |
| Red Haralson | 6.8 | 5.4 | 7.0 | 6.1 | 6.8 | 6.4 |
| Regent | 7.9 | 7.0 | 7.1 | 7.1 | 7.2 | 9.0 |
| William's Pride | 7.6 | 5.6 | 5.9 | 6.4 | 6.4 | 6.2 |
| Connell Red | 6.9 | 4.7 | 5.5 | 5.6 | 6.0 | 5.5 |
| Keepsake | 5.3 | 5.3 | 7.2 | 5.6 | 6.0 | 5.5 |
| 1994 | | | | | | |
| Minnewashta | 7.6 | 6.3 | 7.2 | 7.4 | 7.2 | 7.1 |
| Paulared | 5.6 | 4.8 | 6.2 | 5.3 | 6.7 | 5.3 |
| Sweet Sixteen | 7.5 | 5.8 | 6.9 | 6.7 | 6.3 | 6.8 |

TABLE 1-continued

Sensory Evaluations of Apple Varieties by Trained Panelists. Fruit were harvested at the University of Minnesota Horticultural Research Center. Each variety was rated by 14–20 panelists every year using a scale from 9 = excellent to 1 = very poor for each trait.

| Variety | Appearance | Skin texture | Flesh texture | Flavor | Flesh color | Overall liking |
|---|---|---|---|---|---|---|
| Haralson | 6.8 | 4.9 | 6.1 | 5.4 | 5.8 | 5.2 |
| Regent | 8.0 | 6.8 | 7.6 | 7.4 | 8.8 | 7.7 |
| Honeygold | 6.2 | 6.5 | 7.6 | 7.7 | 7.6 | 7.2 |
| Connell Red | 7.7 | 6.7 | 7.2 | 6.9 | 7.4 | 7.1 |
| 1993 | | | | | | |
| Minnewashta | 6.7 | 6.3 | 7.6 | 7.3 | 7.3 | 7.3 |
| State Fair | 7.3 | 5.3 | 7.2 | 6.3 | 7.7 | 6.6 |
| Paulared | 6.8 | 5.2 | 6.0 | 5.8 | 7.3 | 6.3 |
| Wealthy | 6.6 | 4.8 | 6.1 | 5.4 | 5.9 | 5.4 |
| Sweet Sixteen | 7.5 | 6.8 | 7.3 | 7.2 | 7.1 | 7.2 |
| Honeycrisp | 7.3 | 6.3 | 7.5 | 7.1 | 7.3 | 7.5 |
| Red Haralson | 6.3 | 5.2 | 5.4 | 5.0 | 5.4 | 5.2 |
| Regent | 6.3 | 5.2 | 6.2 | 6.5 | 6.8 | 6.2 |
| 1992 | | | | | | |
| Minnewashta | 7.2 | 5.7 | 5.8 | 5.5 | 7.0 | 6.2 |
| Wealthy | 5.6 | 4.7 | 4.9 | 5.0 | 6.4 | 5.2 |
| Sweet Sixteen | 7.9 | 7.1 | 7.1 | 7.2 | 6.5 | 7.2 |
| Liberty | 7.2 | 6.3 | 6.7 | 6.9 | 7.1 | 6.9 |
| McIntosh (Roger's) | 6.4 | 6.3 | 7.1 | 6.4 | 6.4 | 6.5 |
| Honeycrisp | 7.1 | 7.1 | 7.7 | 7.3 | 6.8 | 7.3 |
| Red Haralson | 6.7 | 5.9 | 6.6 | 6.1 | 6.7 | 6.5 |
| Honeygold | 7.0 | 6.5 | 7.4 | 7.4 | 6.9 | 7.4 |
| Regent | 6.9 | 5.8 | 7.4 | 7.1 | 7.6 | 7.2 |
| Fireside | 6.4 | 6.0 | 6.3 | 6.3 | 6.3 | 6.4 |
| Keepsake | 6.7 | 6.5 | 6.9 | 6.9 | 6.9 | 6.8 |
| 1991 | | | | | | |
| Minnewashta | 7.4 | 6.3 | 5.5 | 6.1 | 6.5 | 5.9 |
| Wealthy | 6.4 | 6.0 | 5.6 | 5.6 | 6.6 | 5.7 |
| Sweet Sixteen | 6.3 | 6.3 | 6.7 | 7.3 | 6.0 | 6.8 |
| McIntosh (Roger's) | 5.3 | 5.8 | 4.6 | 5.9 | 6.9 | 5.5 |
| Honeycrisp | 6.2 | 6.9 | 7.6 | 7.4 | 6.6 | 7.2 |
| Red Haralson | 7.1 | 5.2 | 6.9 | 6.0 | 6.7 | 6.2 |
| Honeygold | 7.0 | 5.8 | 6.4 | 7.4 | 6.6 | 7.1 |
| Regent | 6.7 | 5.0 | 6.7 | 6.1 | 6.7 | 6.1 |
| Fireside | 7.1 | 5.9 | 6.1 | 6.2 | 6.4 | 6.3 |
| 1990 | | | | | | |
| Minnewashta | 5.8 | 6.5 | 7.5 | 7.8 | 7.6 | 7.8 |
| Paulared | 6.4 | 5.3 | 5.0 | 6.1 | 7.1 | 5.8 |
| Honeycrisp | 6.9 | 6.3 | 7.4 | 6.2 | 6.7 | 6.7 |
| Honeygold | 6.8 | 6.1 | 6.1 | 7.0 | 6.8 | 6.7 |
| McIntosh (Roger's) | 6.9 | 5.8 | 5.2 | 5.7 | 6.7 | 5.7 |
| Red Haralson | 6.5 | 6.3 | 6.6 | 5.8 | 6.2 | 5.9 |
| Regent | 7.3 | 5.7 | 7.1 | 6.8 | 7.3 | 6.8 |
| Sweet Sixteen | 6.1 | 6.2 | 6.2 | 6.1 | 5.5 | 6.1 |
| 1989 - No data recorded. | | | | | | |
| 1988 | | | | | | |
| Minnewashta | 5.5 | — | 4.6 | 5.3 | 5.9 | 4.9 |
| Sweet Sixteen | 6.0 | — | 5.5 | 4.8 | 5.0 | 5.2 |
| McIntosh (Roger's) | 5.6 | — | 4.4 | 4.6 | 6.4 | 4.6 |
| Red Haralson | 6.3 | — | 7.3 | 6.8 | 6.8 | 7.0 |
| Regent | 6.8 | — | 6.6 | 6.2 | 5.6 | 6.2 |
| Honeygold | 5.3 | — | 5.4 | 5.3 | 5.6 | 5.1 |
| Fireside | 5.5 | — | 5.5 | 4.9 | 6.1 | 5.5 |
| Connell Red | 6.7 | — | 5.3 | 4.5 | 5.9 | 5.1 |
| 1987 | | | | | | |
| Minnewashta | 5.9 | — | 7.5 | 7.5 | 7.3 | 7.6 |
| Wealthy | 6.3 | — | 6.4 | 5.9 | 6.9 | 6.2 |
| Sweet Sixteen | 6.9 | — | 7.1 | 6.3 | 5.4 | 6.2 |

TABLE 1-continued

Sensory Evaluations of Apple Varieties by Trained Panelists. Fruit were harvested at the University of Minnesota Horticultural Research Center. Each variety was rated by 14–20 panelists every year using a scale from 9 = excellent to 1 = very poor for each trait.

| Variety | Appearance | Skin texture | Flesh texture | Flavor | Flesh color | Overall liking |
|---|---|---|---|---|---|---|
| McIntosh (Roger's) | 7.3 | — | 5.2 | 6.8 | 7.3 | 6.1 |
| Honeycrisp | 6.2 | — | 7.9 | 6.6 | 6.3 | 6.6 |
| Red Haralson | 6.3 | — | 6.7 | 5.4 | 6.6 | 6.0 |
| Regent | 6.5 | — | 7.2 | 6.6 | 7.6 | 6.8 |
| Honeygold | 6.2 | — | 6.4 | 5.3 | 7.0 | 5.6 |
| Fireside | 5.8 | — | 7.0 | 6.8 | 6.9 | 6.7 |
| Connell Red | 6.7 | — | 5.5 | 4.7 | 6.6 | 5.3 |
| 1986 | | | | | | |
| Minnewashta | 6.8 | — | 6.3 | 7.2 | 6.4 | 6.9 |
| State Fair | 6.8 | — | 5.0 | 5.0 | 6.8 | 5.2 |
| Gala | 5.2 | — | 6.2 | 6.2 | 6.3 | 5.9 |
| Wealthy | 6.3 | — | 4.4 | 5.0 | 7.6 | 4.8 |
| McIntosh (Roger's) | 6.7 | — | 3.8 | 4.5 | 7.6 | 4.3 |
| Sweet Sixteen | 6.4 | — | 5.8 | 5.8 | 5.4 | 5.8 |
| Honeycrisp | 6.6 | — | 7.1 | 6.8 | 6.1 | 6.8 |
| Red Haralson | 6.0 | — | 6.3 | 6.9 | 6.5 | 6.3 |
| Regent | 6.0 | — | 5.2 | 6.0 | 6.5 | 5.3 |
| Connell Red | 6.2 | — | 5.8 | 5.1 | 6.0 | 5.4 |
| Keepsake | 6.2 | — | 5.1 | 5.9 | 6.0 | 5.6 |

TABLE 2

Hardiness Ratings. Winter injury ratings for Minnewashta and other cultivars grown at the University of Minnesota Horticultural Research Center.

| Cultivar | 1990 | 1991 | 1992 | 1993 | 1994 | 1995 | 1996 |
|---|---|---|---|---|---|---|---|
| Minnewashta | 4.5 | 4 | 4 | 4.5 | 4 | 4 | 4 |
| Braeburn | — | — | — | — | — | 4 | 3 |
| Cortland (Redcort) | 4 | 4 | 4 | 4 | 4 | 4 | 4 |
| Empire | 3 | 4 | 4 | 4 | 3.5 | 4 | 3.5 |
| Empress | — | 4 | 4 | 4 | 4 | 4 | 4 |
| Freedom | 3.5 | 4 | 4.5 | 3.5 | 4 | 4 | 3.5 |
| Fuji | — | — | — | — | — | 4 | 4 |
| Golden Delicious | 2.5 | 3 | 3 | 3 | 2 | 1 | 0 |
| Haralson (Haralred) | 4 | 5 | 5 | 5 | 5 | 5 | 5 |
| Haralson | 3.5 | 4 | 5 | 4 | 4 | 4 | 4 |
| Honeycrisp | 4 | 4 | 4 | 4 | 4 | 4 | 4 |
| Honeygold | — | 4 | 4 | 4 | 4.5 | 4 | 4 |
| Idared | 4 | 4 | 4 | 4 | 3 | 4 | 3.5 |
| Jerseymac | 3 | 4 | 4 | 4 | 4 | 4 | 4 |
| Melrose | — | 4 | 4 | 4 | 4 | 3.5 | 3.5 |
| Mutsu | 3 | 3.5 | 3.5 | 3.5 | 1 | 2 | 2.5 |
| Jonamac | 4 | 4 | 4 | 3 | 4 | 3 | 4 |
| Jonafree | — | — | — | 4 | 4 | 4 | 3.5 |
| Jonagold | 3 | 4 | 3.5 | 1 | 0 | — | — |
| Jonathan | 4 | 4 | 4 | 4 | 4 | 3 | 3 |
| Liberty | 4 | 4 | 4 | 4 | 4 | 4 | 4 |
| McIntosh (NuRed) | 4 | 4 | 4 | 4 | 4 | 4 | 4 |
| Paulared | 4 | 4 | 4 | 4 | 4 | 4 | 4 |
| Spigold | — | 4 | 4 | 4 | 3 | 3.5 | 2 |
| RedFree | — | — | — | 4 | 4 | 4 | 4 |
| Regent | 4 | 4 | 4 | 4 | 4 | 4 | 4 |
| State Fair | 4 | 5 | 4 | 5 | 4.5 | 4 | 4 |
| Wealthy (Red) | — | 4 | 5 | 4 | 4 | 4 | 4 |
| Sweet Sixteen | 4 | 4 | 4 | 4 | 4 | 4 | 3.5 |

Rating scale ranges from 0 = dead to 5 = no injury. The subjective evaluation performed in July and August from 1990 through 1996, is a composite impression based on vigor of new growth, leaf size and quantity, and the presence and severity of injury to trunk and shoots.

We claim:

1. A new and distinct apple tree substantially as shown and described herein and combining the characteristics of having a somewhat upright form with vigorous growth in early years and attaining a spur-type habit with moderately vigorous growth as it matures, winter hardiness and annual fruit production, with fruit ripening during the early season yet having a long storage life, well-balanced flavor, crisp and juicy texture, and pleasing exterior color and pattern.

* * * * *

UNITED STATES PATENT AND TRADEMARK OFFICE

CERTIFICATE OF CORRECTION

PATENT NO. : PP 11,367
DATED : April 25, 2000
INVENTOR(S) : Luby et al.

It is certified that error appears in the above-identified patent and that said Letters Patent is hereby corrected as shown below:

Column 3,
Line 56, delete "(U.S. Plant Pat. No. 7,167)" and replace with -- (U.S. Plant Pat. No. 7,197) --.

Signed and Sealed this

Twenty-fifth Day of December, 2001

*Attest:*

*Attesting Officer*

JAMES E. ROGAN
*Director of the United States Patent and Trademark Office*